(12) United States Patent
Abrahamson

(10) Patent No.: US 8,369,962 B2
(45) Date of Patent: Feb. 5, 2013

(54) MEDICAL TELEMETRY SYSTEM AND OPERATING METHOD THEREFOR

(75) Inventor: Hans Abrahamson, Stockholm (SE)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 13/239,688

(22) Filed: Sep. 22, 2011

(65) Prior Publication Data
US 2012/0010682 A1    Jan. 12, 2012

Related U.S. Application Data

(62) Division of application No. 12/303,176, filed as application No. PCT/SE2006/000698 on Jun. 9, 2006, now Pat. No. 8,060,213.

(51) Int. Cl.
*A61N 1/00* (2006.01)

(52) U.S. Cl. ............................. 607/60; 607/32

(58) Field of Classification Search .............. 607/30–31, 607/59–60; 128/903
See application file for complete search history.

(56) References Cited

U.S. PATENT DOCUMENTS

| | | | |
|---|---|---|---|
| 6,636,738 B1 * | 10/2003 | Hayashi | ......................... 455/450 |
| 6,801,807 B2 | 10/2004 | Abrahamson | |
| 6,978,081 B1 | 12/2005 | Schulz | |
| 7,218,969 B2 | 5/2007 | Vallapureddy et al. | |
| 7,664,553 B2 | 2/2010 | Roberts | |
| 2001/0023361 A1 | 9/2001 | Pauly et al. | |
| 2002/0103514 A1 | 8/2002 | Abrahamson | |
| 2003/0088295 A1 | 5/2003 | Cox | |
| 2003/0220673 A1 | 11/2003 | Snell | |
| 2004/0120288 A1 * | 6/2004 | Adjakple et al. | ............... 370/333 |
| 2004/0158299 A1 | 8/2004 | Patrias | |
| 2005/0068928 A1 | 3/2005 | Smith et al. | |
| 2005/0250507 A1 | 11/2005 | Leung et al. | |
| 2006/0173444 A1 | 8/2006 | Choy et al. | |
| 2006/0239225 A1 | 10/2006 | Cho et al. | |
| 2008/0015656 A1 * | 1/2008 | Bange et al. | ..................... 607/32 |
| 2008/0046584 A1 * | 2/2008 | Tucker | ......................... 709/231 |

* cited by examiner

*Primary Examiner* — Christopher D Koharski
*Assistant Examiner* — Catherine Voorhees

(57) ABSTRACT

A method in a telemetry system for establishing a connection between a base station and an implantable medical device includes the steps of: starting, in the base station, a first timer B-$T_2$; determining, in the base station 4, channels that are free for communication among a number of available channels, and selecting one of the free channels; starting, in the base station, a second timer; transmitting, as long as the first or second timer has not expired, a recognition message on the selected channel to the implantable medical device; and establishing, upon receipt of a recognition reply message from the implantable medical device, communication between the base station and the implantable medical device on the selected channel. The invention is readily adaptable for fulfillment of different requirements, such as stipulated by the ETSI standard.

7 Claims, 3 Drawing Sheets

MEDICAL TELEMETRY SYSTEM AND OPERATING METHOD THEREFOR

RELATED APPLICATION

The present application is a division of application Ser. No. 12/303,176, filed on Dec. 2, 2008 now U.S. Pat. No.8,060,213 as the National Stage entry for International Application No. PCT/SE2006.00698, having an international filing date of Jun. 9, 2006.

BACKGROUND OF THE INVENTION

1. Field of the Invention

The present invention relates generally to medical implant communication systems, and in particular to methods for a base station and for an implantable medical device in such systems.

2. Description of the Prior Art

In a medical telemetry system an implantable device such as a pacemaker is monitored regularly by an external programming device. A physician treating the patient can thereby obtain important information, for example in order to evaluate the heart activity of the patient. The physician is also able to make changes to the settings of the implantable device if such need arises. In order to accomplish this bidirectional communication, a radio connection has to be set up between the programming device of the telemetry system and the implantable device.

United States Patent Application Publication No. 2003/0220673 is directed to methods for combating interference occurring in a telemetry system and to enabling multiple programmers to communicate with multiple implantable devices. Some aspects of selecting a channel are also discussed. The programmers may for example dynamically store a table and mark channels used by other programmers and devices as reserved, or they may coordinate their use of the telemetry channels.

However, arranging the programmers to coordinate their use of channels is tedious and requires programs, operating parameters and elaborate algorithms for implementing the methods, which thus increases the overall costs of the medical telemetry system. Further, having a pre-arranged channel on which communication is to be conducted entails a number of drawbacks. For example, the pre-arranged channel may not be the channel that is best suited for communication at the time and this is also a rather non-flexible method.

Further, European Standard ETSI EN 301 839-1 defines characteristics that a medical implant communications system (MICS) has to meet. The available spectrum has to be used as efficiently as possible and the document specifies some requirements that have to be fulfilled. These requirements have to be taken into consideration when designing a MICS system and the devices used within the system.

It would thus be desirable to provide an improved method for establishing a connection between a base station and an implantable medical device of a telemetry system. Further, it would be desirable to provide such method, fulfilling the requirements set by the above-mentioned ETSI standard.

SUMMARY OF THE INVENTION

It is an object of the present invention to provide an improved method for allocating a channel in a telemetry system that enables fulfillment of the requirements of the ETSI standard.

It is another object of the present invention to provide a reliable and simple method for establishing a connection between a base station and an implantable medical device.

In accordance with a first aspect of the invention, a method for a base station of a medical telemetry system is provided. In particular, a method for establishing communication between a base station and an implantable medical device of a medical telemetry system is provided. The method includes the steps of: starting, in the base station, a first timer; determining, in the base station, channels that are free for communication among a number of available channels, and selecting one of the free channels; starting, in the base station, a second timer; transmitting, as long as the first or second timer has not expired, a recognition message on the selected channel to the implantable medical device; and establishing, upon receipt of a recognition reply message from the implantable medical device, communication between the base station and the implantable medical device on the selected channel. By means of the invention an improved yet simple method for establishing a connection between a base station and an implantable medical device is provided. The method is readily adaptable to fulfil any requirements put on communication within medical telemetry systems, for example requirements stipulated by the ETSI standards. A very flexible and easily adjustable method is thereby provided.

In accordance with an embodiment of the method, if the second timer has expired while the first timer has not expired and if no recognition reply message is received from the implantable medical device, the steps of: determining and selecting a free channel, starting the second timer and transmitting a recognition message to the implantable medical device are repeated.

In accordance with another embodiment of the invention the step of determining and selecting a free channel includes the sub-steps of: measuring received signal strengths of all available channels and selecting the channel having the lowest signal strength. By means of these sub-steps the channel that is best suited for communication at the time can be chosen.

In accordance with yet another embodiment of the invention, the implantable medical device is a dedicated implantable medical device. In situations such as at a home follow-up system a specific implantable medical device may have to be contacted. Alternatively, a base station may be used in a broadcast mode, whereby all implantable medical devices within communication range can respond and make their presence known.

In accordance with another embodiment of the invention, the first timer is set to a time interval within the range of 5-60 seconds. This is a suitable time interval, during which contact should be established.

In accordance with yet another embodiment of the invention, the second timer is set to a time interval within the range of 1-5 seconds. The ETSI standard specifies the maximum allowable time interval for occupying a channel if no answer is received, and the invention provides means for fulfilling this requirement.

In accordance with yet another embodiment of the invention the method is initiated upon the occurrence of an activating mechanism. For example, the activating mechanism may be a timer indicating a time of day at which an information transfer session is to be conducted. This is particularly suitable for example in a home follow-up system, whereby the transfer session is established regularly and the patient does not need take any actions at all.

In accordance with another embodiment of the invention, the method is halted if the second timer expires. This ensures that the method is not running in an endless loop. The base station may be arranged to repeat the steps after a specified period of time upon failure to establish communication.

In accordance with a second aspect of the invention, a method for an implantable medical device in a medical telemetry system is provided. A method for establishing communication between a base station and an implantable medical device of a medical telemetry system is provided. The method includes the steps of: starting a first timer; listening for signals transmitted from the base station and determining, among a number of channels, channels that are available for communication; setting a channel number to Ch=First−1, wherein First is the lowest channel number of the available channels; starting a second timer; selecting channel Ch=Ch+1 among the available N channels, wherein if Ch≧N+First, then setting Ch=First; listening on the selected channel as long as the first or second timer has not expired and as long as no recognition message has been received; and repeating, as long as the first timer has not expired and no recognition message is received from the base station and the second timer has expired, the steps of: starting the second timer; selecting the channel Ch=Ch+1 among the available N channels and listening on the selected channel; transmitting, upon receipt of a recognition message from the base station, a recognition reply message to the base station. Advantages corresponding to the above are thereby provided.

The invention is further related to a base station and an implantable medical device, respectively, configured to perform the methods.

DESCRIPTION OF THE PREFERRED EMBODIMENTS

In the above mentioned ETSI standard the term "ultra low power active medical implant" (ULP-AMI) is used to denote an implantable medical device within a medical implant communication system or medical telemetry system. In the following description the terms implantable medical device and medical implant are used interchangeably to denote such ULP-AMI. Further, in the standard a device communicating with such ULP-AMI is called a periphery or ULP AMI-P, where the "P" stands for periphery. In the following description a device communicating with an implantable medical device is called a base station, and is intended to denote such ULP AMI-P. Wand, programmer, programmer device and periphery unit are other commonly used equivalent terms for denoting such ULP AMI-P.

Figure 1:
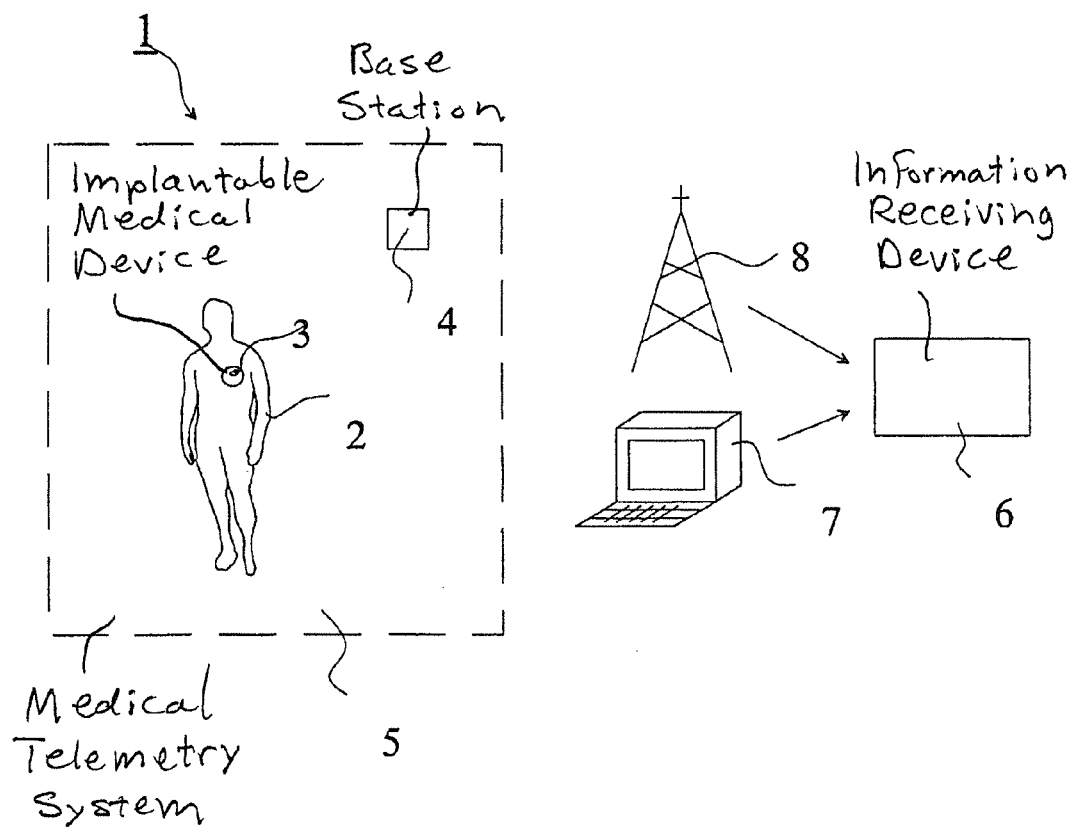
FIG. 1 is a schematic view over a medical implant communication system in which the present invention may be implemented.

FIG. 1 illustrates schematically a medical implant communications system (MICS), in the following denoted medical telemetry system 1. The condition of a patient 2 having an implantable medical device 3 such as a pacemaker can be monitored at his or hers home 5. A base station 4 is provided at the patient's home 5 and information can be transferred to an information receiving device 6 at a hospital or the like. The information receiving device 6 can for example be a computer or a programmer. The transfer of information can be accomplished in any suitable manner, for example over the Internet or over the GMS network, as is schematically illustrated by reference numerals 7 and 8, respectively. In the figure a home-follow up system is illustrated, but it is realized that the present invention may be implemented at a hospital as well.

The present invention provides a method for establishing a connection between an external base station 4 and an implantable medical device 3 of a telemetry system 1. In the present invention it is assumed that no specific radio channel for establishing the connection has been agreed upon in advance, thus avoiding the problems related to using a pre-designated channel. An implantable device 3 that is trying to establish a radio link to the external base station 4 then have to use a search scheme to synchronize its choice of channel with the base station's choice of channel.

In a home follow-up system a periodic dump of patient related information from the implantable medical device 3 to the base station 4 can be scheduled to take place on a regular basis. For example, the information transfer can be made under a certain time interval every night, once a week or once a month depending on the needs of the patient. The ETSI standard EN 301 839-1 referenced to in the introductory part of the present application specifies that a channel to be used for such a data dump must first be assessed and found to be free for use before actually using it. The implantable medical device 3 can thus not just begin sending over a predetermined channel, since it must first listen and assess that a channel is indeed free for use and thereafter pick it. Correspondingly, the ETSI standard requires the base station 4 to perform a listen before talk assessment and then pick a channel. However, the implantable medical device 3 is unaware of which channel is selected by the base station 4, since this choice changes from time to time.

To initiate radio communication the implantable medical device 3 and the base station 4 have to be activated by an activation mechanism. Some activation mechanisms are mentioned in the following, but it is realized that other mechanisms can be utilized as well. The implantable medical device 3 and the base station 4 may have been set up by pre-programming a timing mechanism so that both the implantable medical device 3 and the base station 4 know at what time $T_1$ a transfer session is scheduled to take place. For example, the transfer session may be scheduled to be performed at 11 pm every day. Further, they should be preprogrammed to know a time interval $T_2$, for example one minute, during which the transfer session is supposed to take place.

Alternatively, an external activating system may be utilized, for example some external mechanism such as an external magnet providing a magnetic field activating the transmit function of the implantable medical device, inductive loop telemetry or other radio alert systems operating in other bands.

When a chosen activation mechanism occurs then the implantable medical device 3 is said to be triggered for a communication channel search. Preferably, the base station is preprogrammed also to know with which implantable medical device 3 to communicate with; in such case the implantable medical device 3 is said to be a dedicated implantable medical device. Further, the base station 4 and the implantable medical device 3 are both preferably preprogrammed so as to know all essential communication properties that have to be fulfilled for a successful link to be established, with the exception of which channel to use.

Figure 2:
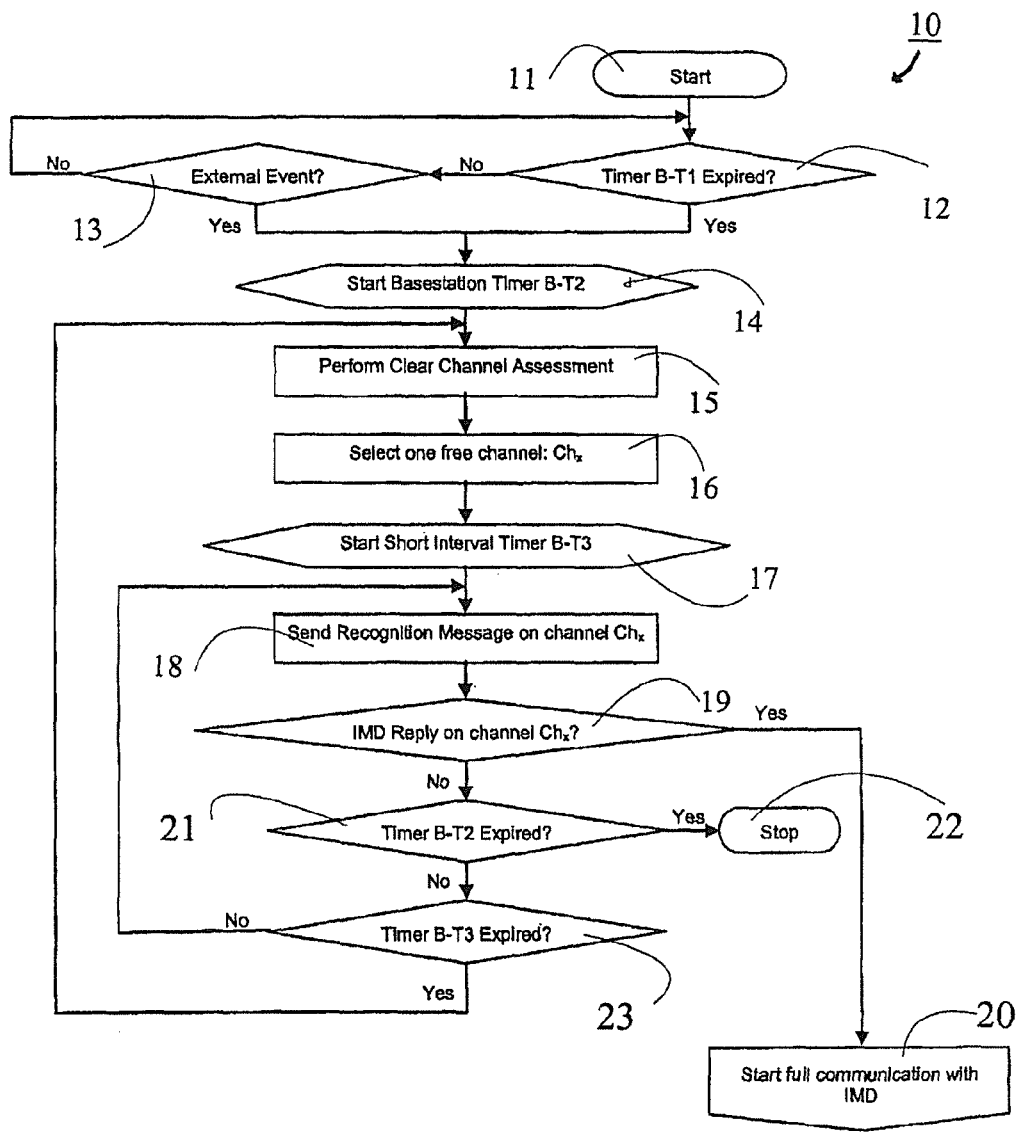
FIG. 2 is a flow chart illustrating the steps of a first embodiment of the method in accordance with the present invention.

FIG. 2 illustrates a flow chart over the steps included in a method in accordance with a first aspect of the present invention. The base station 4 is configured to perform the steps as shown in FIG. 2. More specifically, the base station 4 comprises, among other things, a suitable processor and timers B-T$_2$ and B-T$_3$.

The start of the method 10 is indicated by the box 11. If either an external event has occurred, box 13, or a timer B-T$_1$ indicates a scheduled point of time, box 12, the base station 4 is triggered for executing the following steps.

In step 14, the base station 4 starts a timer B-T$_2$ for counting the session length T$_2$, which can be a few seconds up to a few minutes. The timer B-T$_2$ is in a preferred embodiment set within the range of 5-10 seconds up to 1 minute, but it is realized that other time intervals may be used. Further, in accordance with the invention, the time intervals can easily be changed should such need arise.

Next, in step 15, the base station 4 performs a Clear Channel Assessment. That is, the base station 4 listens for a free channel among all available channels. Such Clear Channel Assessment is required by the above-mentioned ETSI standard.

Then, in step 16, the base station 4 selects one of the free channels, Ch$_x$. Preferably, the channel with the lowest signal activity among the free channels is chosen. The choice of channel can be made in any suitable manner, for example the channel having the lowest received signal strength can be chosen.

When a channel Ch$_x$ has been chosen the base station 4 starts a second timer B-T$_3$, step 17. This timer is a short interval timer, the interval being within the range of 1-5 seconds. In the ETSI standard restrictions are put on this time interval, and 5 seconds is the maximum time allowed to occupy a channel if no answer is received.

The base station 4 then sends a recognition message on the chosen channel Ch$_x$, step 18. If, in step 19, the implantable medical device 3 replies on the channel Ch$_x$ then full communication is initiated between the base station 4 and the implantable medical device 3, and the method ends at step 20. If on the other hand the implantable medical device 3 fails to reply then the base station 4 checks if the timer B-T$_2$ has expired, step 21. If this timer has expired the communication establishment procedure is halted, step 22. In case a communication establishment fails, the base station can be arranged to repeat the steps of the method after a specific time period. Further, upon failure an error message may be sent to a monitoring center.

If the timer B-T$_2$ has not expired, then the base station 4 checks if the timer B-T$_3$ has expired, step 23. If the timer has not expired then the base station 4 sends another recognition message on the chosen channel Ch$_x$, and the steps 18-23 are repeated. If the second timer B-T$_3$ has expired the base station 4 performs a new Clear Channel Assessment, and the method is repeated starting from step 15. As soon as an implantable medical device 3 returns a recognition reply message a communication dialog is started between the base station 4 and the implantable medical device 3 on the chosen channel Ch$_x$.

Figure 3:
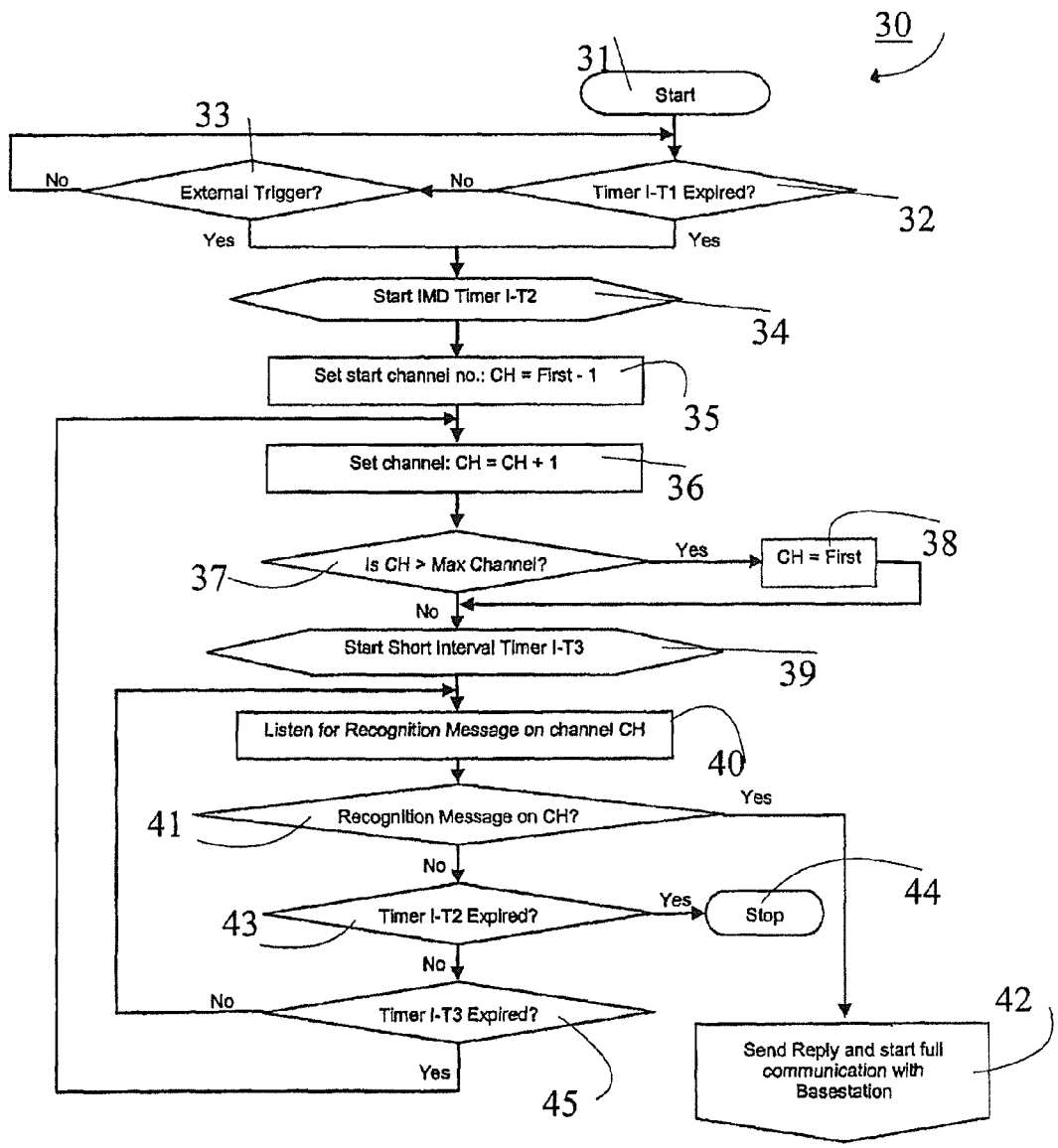
FIG. 3 is a flow chart illustrating the steps of a second embodiment of the method in accordance with the present invention.

FIG. 3 illustrates the corresponding steps performed by an implantable medical device 3. The implantable medical device 3 is configured to perform the steps as shown in FIG. 3. More specifically, the implantable medical device 3 has, among other things, a suitable processor and timers I-T$_2$ and I-T$_3$.

The start of the method 30 is indicated by the box 31. If either an external event has occurred, box 33, or a timer I-T$_1$ indicates a scheduled point of time, box 32, then the implantable medical device 3 is triggered for executing the following steps.

The timer I-T$_2$ is started for counting the session length T$_2$, step 34. The session length could be any suitable time interval, for example up to a few minutes. The channel number is set to Ch=First−1 in step 35, where First is the lowest channel number among the free channels. Thereafter, in step 36, the channel is set to Ch=Ch+1. In step 37, a check is performed to establish whether the current channel number is larger than the maximum allowed channel number. If yes, then Ch is set to First in step 38. If the channel number is not larger than the highest allowed channel number then a short interval timer I-T$_3$ is started in step 39. This time interval may be set to any suitable length, for example within the range of 10-100 ms.

The implantable medical device 3 thereafter listens for a recognition message on the set channel Ch, step 40. If, in step 41, a recognition message is received on the channel Ch then the implantable medical device 3 sends a recognition reply message to the base station 4 and full communication is initiated between the base station 4 and the implantable medical device 3, in step 42. If no recognition message is received on the channel Ch, then a check is made as to whether the timer I-T$_2$ has expired, step 43. If the timer has expired then the method is halted in step 44. The implantable medical device 3 may be arranged to initiate another attempt at obtaining contact with the base station 4, for example after a specified period of time.

If the first timer I-T$_2$ has not expired then the implantable medical device 3 checks if the second timer I-T$_3$ has expired, step 45. If the timer I-T$_3$ has not expired then the implantable medical device 3 continues to listen on the channel Ch for a recognition message and the steps 40-45 are repeated. If the second timer I-T$_3$ has expired, then the implantable medical device 3 proceeds by listening to the next available channel in step 36, and the steps starting from step 36 are repeated.

As soon as an implantable medical device 3 receives a recognition message from the base station 4 on a channel Ch, then a communication dialog is started between the base station 4 and the implantable medical device 3 on this channel Ch.

The base station may be arranged to try to establish a radio connection to a specific, dedicated implantable medical device. Alternatively, the methods as described above could be utilized for a broadcast scenario, for example in order to determine the identity of implantable medical devices that are within communication range of that particular base station.

In summary, the methods in accordance with the present invention are readily set so as to fulfill the different requirements put on a medical telemetry system. Further, the methods in the base station and implantable medical device, respectively, are easily adjustable should the requirements change. Very flexible and easily adjustable methods are thereby provided.

Although modifications and changes may be suggested by those skilled in the art, it is the intention of the inventor to embody within the patent warranted heron all changes and modifications as reasonably and properly come within the scope of his contribution to the art.

I claim as my invention:

1. Method in a telemetry system for allocating a channel for use in communication between an implantable medical device and a base station of said telemetry system, comprising performing, in said implantable medical device, the steps of:
   starting a first timer;
   listening for signals transmitted from said base station and determining, among a number of channels, N channels that are free for communication;
   setting a channel number to wherein First is the lowest channel number of said free channels;
   starting a second timer;

selecting channel among the available N channels;

listening on said selected channel as long as said first timer or second timer has not expired and as long as no recognition message has been received;

repeating, as long as said first timer has not expired and no recognition message is received from said base station and said second timer has expired, said steps of:

starting the second timer, selecting a next channel among the available N channels and listening on said selected channel; and transmitting, upon receipt of a recognition message from said base station, a recognition reply message to said base station.

2. The method as claimed in claim 1, comprising employing a dedicated implantable medical device as said implantable medical device.

3. The method as claimed in claim 1, comprising setting said first timer to a time interval within a range of 10-60 seconds.

4. The method as claimed in claim 1, comprising setting said second timer to a time interval within a range of 10-100 ms.

5. The method as claimed in claim 1, comprising initiating said method upon an occurrence of an activating mechanism.

6. The method as claimed in claim 5, comprising employing an external activating mechanism as said activating mechanism.

7. The method as claimed in claim 6, wherein said external activating mechanism comprises one of a magnet, inductive loop telemetry, and other radio alert system.

* * * * *